(12) United States Patent
Arjunan et al.

(10) Patent No.: US 9,670,176 B2
(45) Date of Patent: Jun. 6, 2017

(54) PROCESS FOR THE PREPARATION OF ZILEUTON

(71) Applicant: Strides Shasun Limited, Chennai (IN)

(72) Inventors: Sankar Arjunan, Chennai (IN); Ramu Dhanapal, Salem (IN); Santha Kumar, Chennai (IN); Aramanai Lakshmanan Srinivasan, Kumbakonam (IN); Krishnan Devendra Prasad, Dharmapuri (IN)

(73) Assignee: Strides Shasun Limited, Chennai (IN)

( * ) Notice: Subject to any disclaimer, the term of this patent is extended or adjusted under 35 U.S.C. 154(b) by 0 days.

(21) Appl. No.: 15/193,385

(22) Filed: Jun. 27, 2016

(65) Prior Publication Data

US 2016/0376251 A1 Dec. 29, 2016

(30) Foreign Application Priority Data

Jun. 27, 2015 (IN) ............... 3250/CHE/2015

(51) Int. Cl.
*C07D 333/58* (2006.01)

(52) U.S. Cl.
CPC ................. *C07D 333/58* (2013.01)

(58) Field of Classification Search
CPC .................................................. C07D 333/58
USPC ....................................................... 549/58
See application file for complete search history.

(56) References Cited

U.S. PATENT DOCUMENTS

| 4,873,259 A | 10/1989 | Summers, Jr. et al. |
| 6,080,874 A | 6/2000 | Hengeveld et al. |

FOREIGN PATENT DOCUMENTS

| IN | 1592/KOL/2007 A | 6/2009 |
| IN | 2307/CHE/2009 A | 4/2011 |

OTHER PUBLICATIONS

Stewart et al., "N,O-Bis(phenoxycarbonyl)hydroxylamine: A New Reagent for the Direct Synthesis of Substituted N-Hydroxyureas", Journal of Organic Chemistry, 1992, pp. 5020-5023, vol. 57.
Wayne et al., "Synthesis of a 5-Substituted Benzo[b]thiophene", Heterocycles, 2000, pp. 1175-1182, vol. 53 No. 5.

*Primary Examiner* — Taofiq A Solola
(74) *Attorney, Agent, or Firm* — The Webb Law Firm

(57) ABSTRACT

The invention discloses a process for the preparation of Zileuton of formula I by employing acetic acid-1-benzo[b]thiophen-2-yl-ethyl-ester of formula-III as an intermediate.

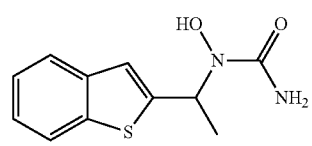

I

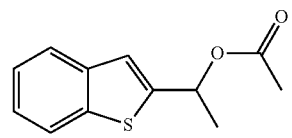

III

20 Claims, 1 Drawing Sheet

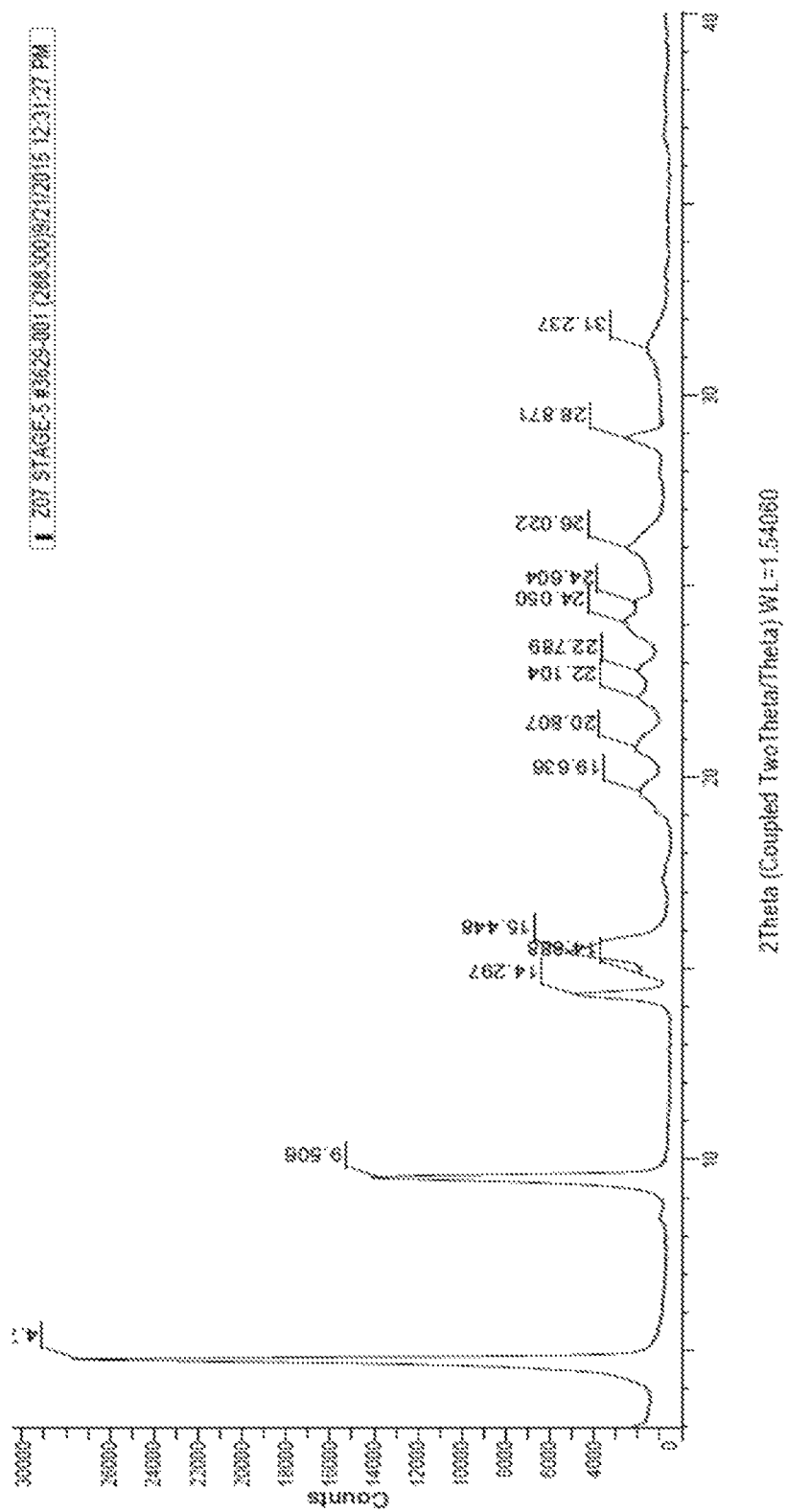

PROCESS FOR THE PREPARATION OF ZILEUTON

CROSS-REFERENCE TO RELATED APPLICATION

This application claims priority to Indian Patent Application No. 3250/CHE/2015 filed Jun. 27, 2015, the disclosure of which is hereby incorporated in its entirety by reference.

FIELD OF THE INVENTION

The present invention relates to a novel process for the preparation of Zileuton of formula I by employing the acetic acid-1-benzo[b]thiophen-2-yl-ethyl-ester of formula-III as an intermediate.

BACKGROUND OF THE INVENTION

Zileuton is chemically known as (±)-N-hydroxy-N-(1-benzo-[b]-thien-2-ylethyl)urea and is mentioned below.

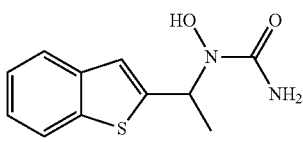

Zileuton is commercially available in USA under the brand name of "Zyflo" an oral tablet for the prophylaxis and chronic treatment of asthma.

Zileuton was first disclosed in the U.S. Pat. No. 4,873,259 (hereinafter read as US '259). The Patent US '259 describes the below mentioned scheme for the preparation of Zileuton.

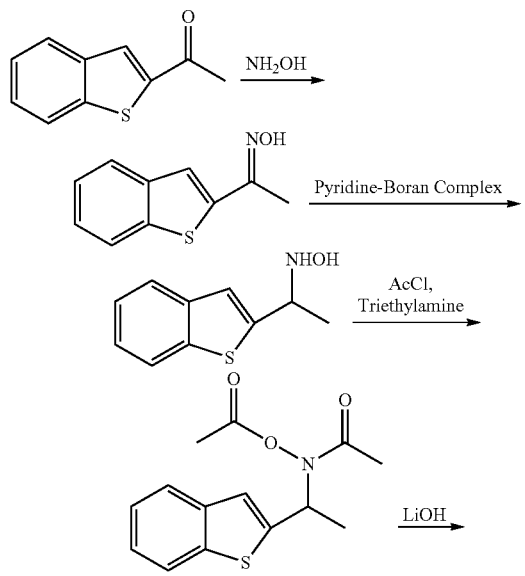

Scheme-1

The aforementioned process employs Pyridine-Borane Complex that is toxic and expensive. Excessive reducing agent required to reduce the oxime increases the cost on a large scale. The U.S. Pat. No. 6,080,874 discloses an alternative process for the preparation of Zileuton in a single step, comprising reacting 1-Benzo[b]thiophen-2-ylethanol of formula-II with hydroxyurea in presence of an acid as mentioned below.

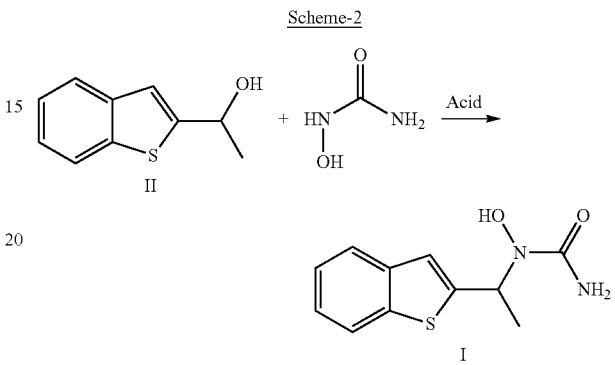

Scheme-2

The process involves the cumbersome purification process due to the high impurity content in Zileuton.

The Indian Patent application IN 1592/KOL/2007 discloses the improved alternate process for the preparation of Zileuton in a single step involving the step of reacting 1-Benzo[b]thiophen-2-ylethanol of formula-II with hydroxyurea in presence of a Lewis acid and Lewis acid is preferably Borontrifluoride diethyletherate.

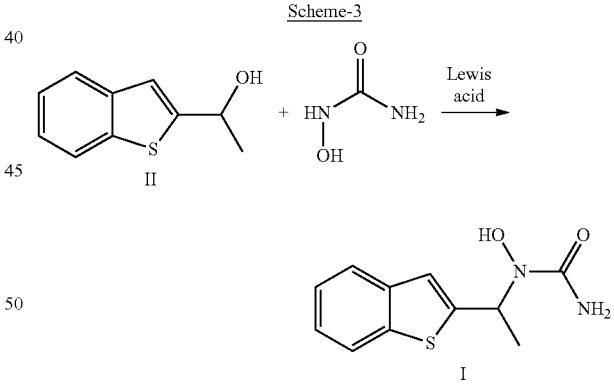

Scheme-3

The Zileuton formed in acidic condition during the reaction of 1-Benzo[b]thiophen-2-ylethanol of formula-II with hydroxyurea results in the below mentioned impurities.

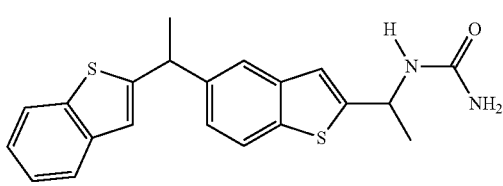

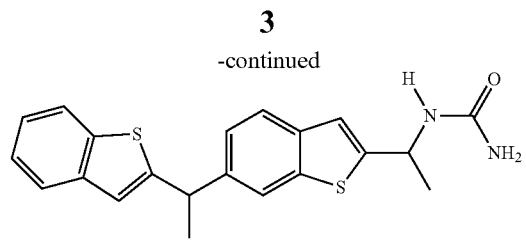

These impurities are difficult to remove from the final Zileuton and also decrease the yield of the final API.

The other process for the preparation of Zileuton disclosed in the publication of Stewart and Brooks in Journal of Organic Chemistry. 1992, 57, 5020-5023, involves the steps of reacting 1-Benzo[b]thiophen-2-ylethanol formula-II with N,O-bis(phenoxycarbonyl)-hydroxylamine in the presence of diisopropylazodicarboxylate (DIAD) and triphenylphosphine to obtain N,O-bis(phenoxycarbonyl)-N-(1-benzo[b]thien-2-yl-ethyl)-hydroxylamine; followed aminolysis in t-butanol as depicted below.

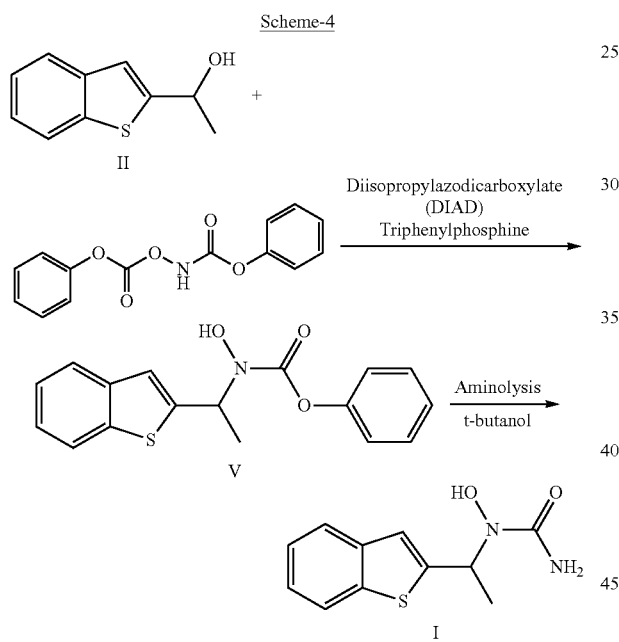

This process is difficult to perform in large scale and the resulting product has to be purified by chromatography to get pure Zileuton. Further reagents such as diisopropylazodicarboxylate and triphenylphosphine are not suitable for large scale preparations.

The publication Heterocycles, vol-53, No-5, 2000, pages 1175-1182 discloses a reaction 1-Benzo[b]thiophen-2-ylethanol of formula-II with phenol in the presence of Boron trifluoride-diethyletherate as depicted below, Scheme-5

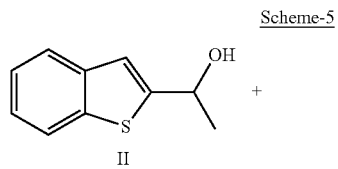

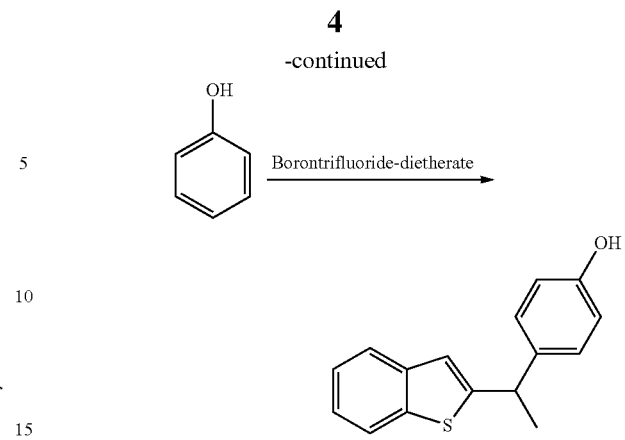

The chromatographic purification of the resulted compound afforded 56% yield and the reactions with similar compounds did not provide desired results.

The Indian Patent application IN 2307/CHE/2007 discloses the preparation for the preparation of Zileuton in two steps involving (1) reaction of 1-Benzo[b]thiophen-2-ylethanol of formula-II with N-(phenoxycarbonyl)-hydroxylamine in presence of hydrochloric acid in toluene to form an intermediate of formula-IV and (2) aminolysis of intermediate of formula-IV in methanol to obtain Zileuton.

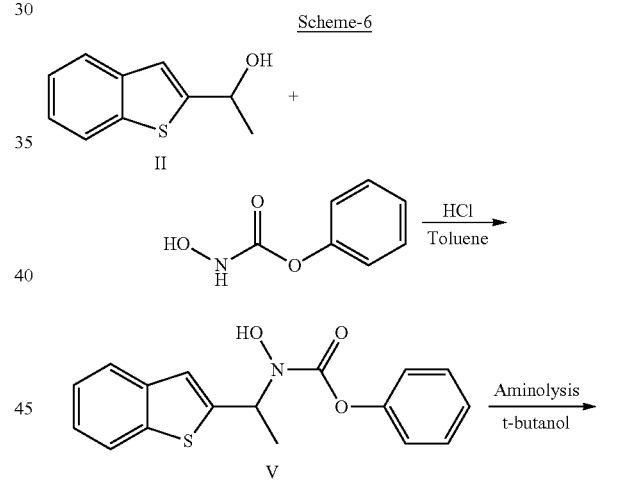

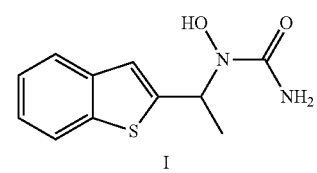

The reaction of 1-Benzo[b]thiopen-2-ylethanol of formula-II with N-(phenoxycarbonyl)-hydroxylamine in presence of hydrochloric acid in toluene at a temperature of 50-55° C. for 5 hrs causes acid degradation of the intermediate of formula-V that decrease the yield of the product.

Therefore, there exists a need for a novel process for the preparation of Zileuton that is simple and efficient in large scale and does not require cumbersome purification of the final API.

SUMMARY OF THE INVENTION

An aspect of the present invention provides a process for preparing Zileuton of formula-I

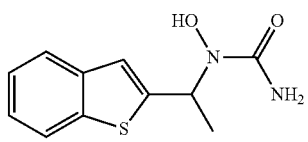

I comprising the steps of;
(i) reacting 1-benzo[b]thiophen-2-yl-ethanol compound of formula II

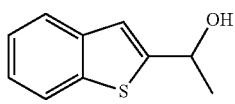

II with anhydride of general formula (RCO)₂O or acid chloride of general formula (RCOX) to obtained 1-benzo[b]thiophen-2-yl-ethyl-ester of formula-III,

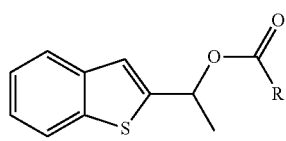

III in presence of suitable base and non-polar aprotic solvent, wherein R is methyl, ethyl or phenyl preferably methyl and X is halogen such as fluoride, chloride, bromide and iodide preferably chloride, (ii) reacting 1-benzo[b]thiophen-2-yl-ethyl-ester compound of formula-III with phenyl-N-hydroxy carbamate of formula-IV,

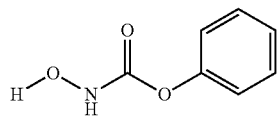

IV in the presence of a Lewis acid to obtain phenyl-1-(benzo[b]thiophen-2-yl)ethyl(hydroxyl) carbamate of formula V,

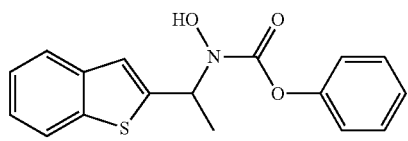

V (iii) optionally purifying the compound of formula V using a suitable solvent to provide pure phenyl-1-(benzo[b]thiophen-2-yl)ethyl(hydroxyl)carbamate of formula V, and (iv) treating phenyl-1-(benzo[b]thiophen-2-yl)ethyl(hydroxyl)carbamate compound of formula-V with ammonia to obtain Zileuton of formula I.

Another aspect of the invention provides a process for preparing Zileuton of formula-I comprising the steps of;
(i) treating phenyl-1-(benzo[b]thiophen-2-yl)ethyl(hydroxyl)carbamate of formula-V,

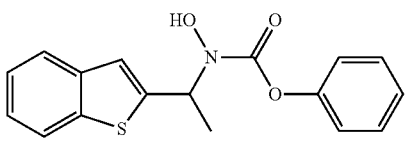

V with ammonia in dimethylformamide as a solvent.

Still another aspect of the invention provides a process for preparing Zileuton of formula-I comprising the steps of:
(i) treating phenyl N, O-Bis(phenoxycarbonyl)-N-(1-benzo[b]thien-2-ylethyl) hydroxylamine of formula Va as mentioned below,

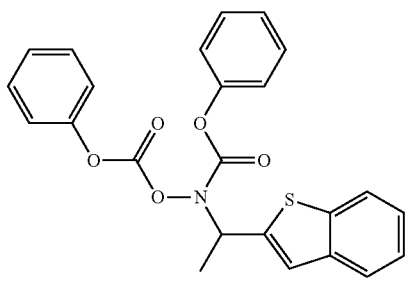

Va with ammonia in dimethyl formamide as a solvent.

Yet another aspect of the invention provides a process for preparing the compound of phenyl-1-(benzo[b]thiophen-2-yl) ethyl (hydroxyl) carbamate of formula-V as mentioned below

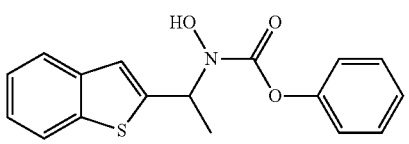

V comprising the steps of;
(i) reacting acetic acid-1-benzo[b]thiophen-2-yl-ethyl-ester of formula-III

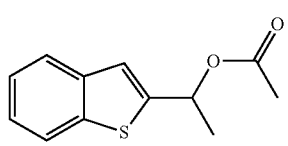

III with phenyl-N-hydroxy carbamate of formula-IV,

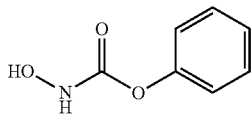

in the presence of a Lewis acid to obtain phenyl-1-(benzo[b]thiophen-2-yl)ethyl(hydroxyl)carbamate of formula-V.

Still another aspect of the invention provides a process for preparing phenyl N, O-Bis(phenoxycarbonyl)-N-(1-benzo[b]thien-2-ylethyl) hydroxylamine of formula Va

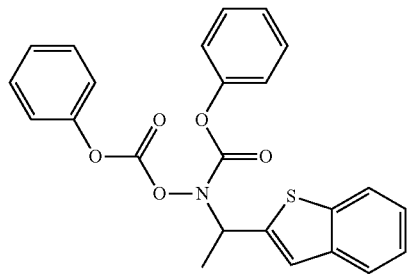

comprising the steps of;
(i) reacting the acetic acid-1-benzo[b]thiophen-2-yl-ethyl-ester of formula-III

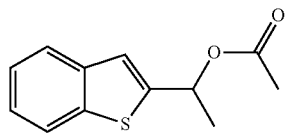

with N, O-Bis-(phenoxy carbonyl) hydroxyl-amine of formula-IVa,

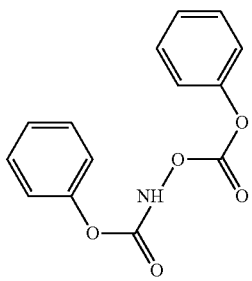

in the presence of a Lewis acid to obtain phenyl N, O-Bis(phenoxycarbonyl)-N-(1-benzo[b]thien-2-yl-ethyl) hydroxylamine of formula Va.

BRIEF DESCRIPTION OF THE DRAWING

FIG. 1 illustrates the powder X-ray Diffractograms of crystalline Zileuton.

DETAILED DESCRIPTION OF THE INVENTION

One embodiment of the present invention provides an improved process for the preparation of Zileuton, compound of formula-I, which comprises of the following steps;
(i) reacting the compound of formula III

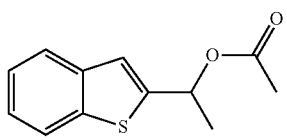

with phenyl N-hydroxy carbamate compound of formula IV,

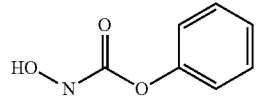

in a suitable solvent in the presence of Lewis acid to produce the compound of formula V,

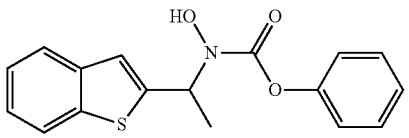

(ii) optionally purifying the compound of formula V using a suitable solvent to provide pure of compound of formula V, and
(iii) reacting the compound of formula V with ammonia in the presence of polar aprotic solvent to provide Zileuton, compound of formula I.

The suitable solvent in step (i) of the embodiment is selected from the group comprising benzene, toluene, xylene, tetrahydrofuran, 2-methyltetrahydrofuran preferably toluene and The Lewis acid in step (i) of the embodiment is selected from the group comprising aluminum bromide, aluminum chloride, boron trifluoride, boron trichloride, boron trifluoride-diethyletherate, boron tribromide, titanium tetrachloride, titanium tetrabromide, stannic chloride, stannic bromide, bismuth trichloride, ferric chloride preferably boron trifluoride-diethyletherate.

The suitable solvent in step (ii) of the embodiment is selected from the group comprising hexane, cyclohexane, benzene, toluene, xylene, tetrahydrofuran, preferably cyclohexane.

The polar aprotic solvent in step (iii) of the embodiment is selected from the group comprising Dimethylformamide, acetone, ethyl acetate, tetrahydrofuran, acetonitrile, dimethylsulfoxide, nitromethane, propylene carbonate preferably dimethylformamidein presence or absence of water.

The second embodiment of the present invention provides an improved process for the preparation of Zileuton, compound of formula-I, which comprises of the following steps;

(i) reacting the compound of formula III

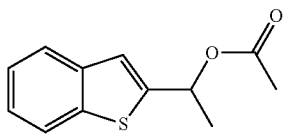

III with N,O-Bis-(phenoxy carbonyl)hydroxyl amine compound of formula IVa,

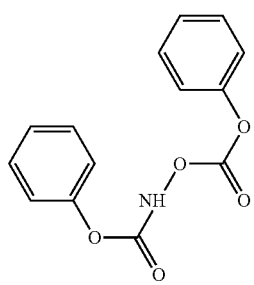

IVa in a suitable solvent in the presence of Lewis acid to produce the compound of formula Va,

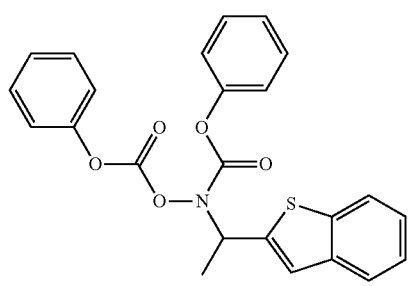

Va (ii) optionally purifying the compound of formula Va using a suitable solvent to provide pure of compound of formula Va and
(iii) reacting the compound of formula Va with ammonia in the presence of polar aprotic solvent to provide Zileuton, compound of formula I.

The suitable solvent in step (i) of the embodiment is selected from the group comprising benzene, toluene, xylene, tetrahydrofuran, 2-methyltetrahydrofuran preferably toluene.

The Lewis acid in step (i) of the embodiment is selected from the group comprising aluminum bromide, aluminum chloride, boron trifluoride, boron trichloride, boron trifluoride-diethyletherate, boron tribromide, titanium tetrachloride, titanium tetrabromide, stannic chloride, stannic bromide, bismuth trichloride, ferric chloride preferably boron trifluoride-diethyletherate.

The suitable solvent in step (ii) of the embodiment is selected from the group comprising hexane, cyclohexane, benzene, toluene, xylene, tetrahydrofuran, preferably cyclohexane.

The polar aprotic solvent in step (iii) of the embodiment is selected from the group comprising Dimethylformamide, acetone, ethyl acetate, tetrahydrofuran, acetonitrile, dimethylsulfoxide, nitromethane, propylene carbonate preferably dimethylformamide in presence or absence of water.

In third embodiment of the present invention provides an improved process for the preparation of Zileuton, compound of formula-I,

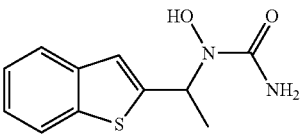

I comprising the steps of:
(i) reacting 1-benzo[b]thiophen-2-yl-ethanol compound of formula II

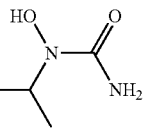

II with anhydride of general formula $(RCO)_2O$ or acid chloride of general formula (RCOX) in presence of suitable base and non-polar aprotic solvent to provides 1-benzo[b]thiophen-2-yl-ethyl-ester of compound of formula-III,

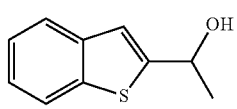

III wherein R is methyl, ethyl or phenyl preferably methyl and X is halogen such as Fluoride, chloride, bromide and iodide preferably chloride,
(ii) reacting the compound of formula III with phenyl N-hydroxy carbamate compound of formula IV,

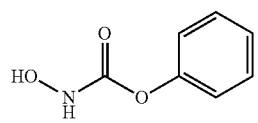

IV in a suitable solvent in the presence of Lewis acid to produce the compound of formula V,

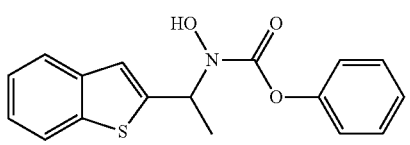

V (iii) optionally purifying the compound of formula Va using a suitable solvent to provide pure of compound of formula Va, and (iv) reacting the compound of formula V with ammonia in the presence of polar aprotic solvent to provide Zileuton, compound of formula I.

The suitable base in step (i) of the embodiment is selected from the group comprising triethyl amine, pyridine, dimethylaminopyridine (DMAP), preferably dimethylaminopyridine (DMAP).

The suitable non-polar aprotic solvent in step (i) of the embodiment is selected from the group comprising benzene, toluene, xylene, tetrahydrofuran, 2-methyltetrahydrofuran preferably toluene.

The Lewis acid in step (ii) of the embodiment is selected from the group comprising aluminum bromide, aluminum chloride, boron trifluoride, boron trichloride, boron trifluoride-diethyletherate, boron tribromide, titanium tetrachloride, titanium tetrabromide, stannic chloride, stannic bromide, bismuth trichloride, ferric chloride preferably boron trifluoride-diethyletherate.

The suitable solvent in step (iii) of the embodiment is selected from the group comprising hexane, cyclohexane, benzene, toluene, xylene, tetrahydrofuran, preferably cyclohexane.

The polar aprotic solvent in step (iv) of the embodiment is selected from the group comprising Dimethylformamide, acetone, ethyl acetate, tetrahydrofuran, acetonitrile, dimethylsulfoxide, nitromethane, propylene carbonate preferably dimethylformamide in presence or absence of water.

Unexpectedly the inventors of the present invention found the use of Lewis acid increases the rate of reaction wherein the reaction is completed in a short period of time thereby decreasing the percentage of impurity formation than the prior arts.

The use of boron trifluoride-diethyletherate as Lewis acid in step (ii) has resulted in preparation of compound of formula V and Va having a purity of greater than 99%. Moreover, it was also observed the inventors that by employing the compound of formula III, the reaction between the compound of formula III and compound of formula V or Va proceed without the formation of/generation of hydrolyzed product compound III or the compound of formula II.

The fourth embodiment of the present invention provides an improved process for the preparation of acetic acid-1-benzo[b]thiophen-2-yl-ethylester compound of formula III,

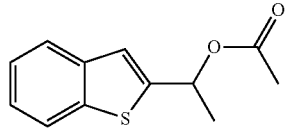

III which comprises of the following steps;
(i) Treating 1-(benzo[b]thiophen-2-yl)ethanol compound of formula-II,

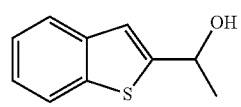

II with acetic anhydride in the presence of acylation catalyst and non-polar aprotic solvent, to provide acetic acid 1-benzo[b]thiophen-2-yl-ethyl ester, compound of formula-III.

The acylation catalyst of the embodiment in step (i) is 4-dimethylaminopyridine and non-polar aprotic solvent which includes but not limited to benzene, toluene, xylene, tetrahydrofuran, 2-methyltetrahydrofuran preferably toluene.

4-Dimethylaminopyridine is a derivative of pyridine and used as nucleophilic catalyst for a variety of reactions such as esterification with anhydrides.

The fifth embodiment of the present invention provides a process for preparing the compound of phenyl-1-(benzo[b]thiophen-2-yl)ethyl(hydroxyl)carbamate of formula-V

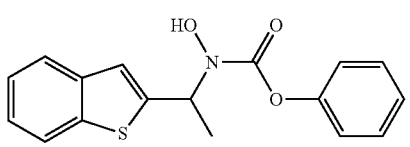

V comprising the steps of;
(i) reacting the acetic acid-1-benzo[b]thiophen-2-yl-ethyl-ester of formula-III

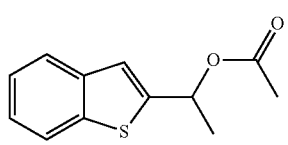

III with phenyl-N-hydroxy carbamate of formula-IV,

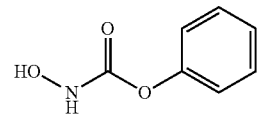

IV in the presence of a Lewis acid to obtain phenyl-1-(benzo[b]thiophen-2-yl)ethyl(hydroxyl)carbamate of formula-V.

The Lewis acid of the embodiment is selected from the group comprising aluminum bromide, aluminum chloride, boron trifluoride, boron trichloride, boron trifluoride-diethyletherate, boron tribromide, titanium tetrachloride, titanium tetrabromide, stannic chloride, stannic bromide, bismuth trichloride, ferric chloride preferably boron trifluoride-diethyletherate.

The sixth embodiment of the present invention provides process for preparing the compound of phenyl N, O-Bis (phenoxycarbonyl)-N-(1-benzo[b] thien-2-ylethyl) hydroxylamine of formula Va comprising the steps of;
(i) reacting acetic acid-1-benzo[b]thiophen-2-yl-ethyl-ester of formula-III

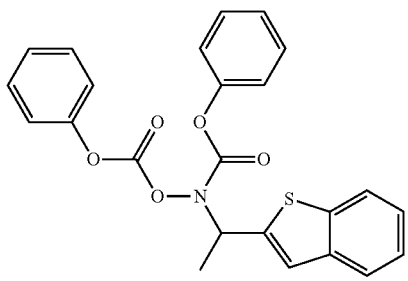

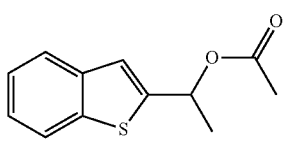

with N, O-Bis-(phenoxy carbonyl) hydroxyl-amine of formula-IVa,

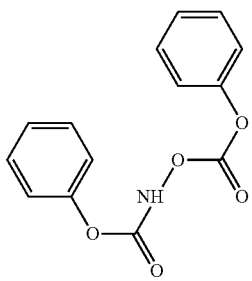

in the presence of a Lewis acid to obtain phenyl N, O-Bis(phenoxycarbonyl)-N-(1-benzo[b]thien-2-yl-ethyl) hydroxylamine of formula Va.

The Lewis acid of the embodiment is selected from the group comprising aluminum bromide, aluminum chloride, boron trifluoride, boron trichloride, boron trifluoride-diethyletherate, boron tribromide, titanium tetrachloride, titanium tetrabromide, stannic chloride, stannic bromide, bismuth trichloride, ferric chloride preferably boron trifluoride-diethyletherate.

The seventh embodiment of the present invention provides a process for preparing Zileuton of formula-I comprising the steps of;
(i) treating phenyl-1-(benzo[b]thiophen-2-yl)ethyl(hydroxyl)carbamate of formula-V,

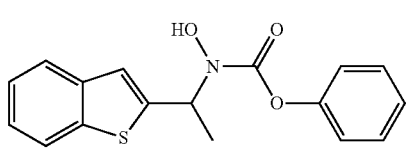

with ammonia in dimethyl formamide as a solvent in presence or absence of water.

The eight embodiment of the present invention provides a process for preparing Zileuton of formula-I comprising the steps of;
(i) treating phenyl N, O-Bis(phenoxycarbonyl)-N-(1-benzo[b]thien-2-ylethyl) hydroxylamine of formula Va

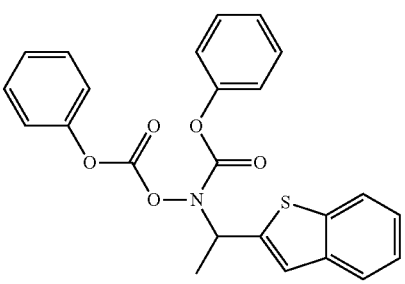

with ammonia in dimethyl formamide as a solvent in presence or absence of water.

Surprisingly the inventors of the present invention have extensively studied the effectiveness of dimethylformamide solvent during the preparation of Zileuton which avoids multiple purifications for the removal of impurities thereby enhancing the yield of Active Pharmaceutical Ingredient.

The Zileuton prepared by the process of present invention provides compound of formula I having a HPLC purity of >99.00 or more preferably 99.90%.

In another embodiment the Zileuton API prepared by process of present invention is further micronized or milled to get the desired particle size. The Zileuton API prepared by process of present invention is has particle size of D (10); 2-5 μm, D (50); 15-25 μm and D (90) 60-75 μm.

The advantages of the present process of invention includes

The process of the present invention does not involve use of toxic or hazardous reagent such as diisopropyl azodicarboxylate, Provides Zileuton with high yield and purity greater than 99.9%

Industrially feasible and scale up able process.

Free from impurities such as N-(1-benzo[b]thien-2-ylethyl)urea, 1-benzo-[b]thien-2-ylethanone and 2-(benzo[b] thien-2-oyl)benzo[b] thiophene.

The present invention is schematically represented by the following scheme and does not limit scope of the invention.

Scheme 1

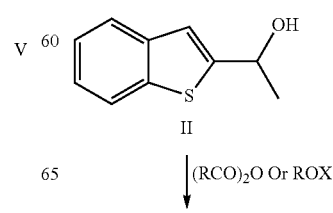

↓ (RCO)₂O Or ROX

-continued

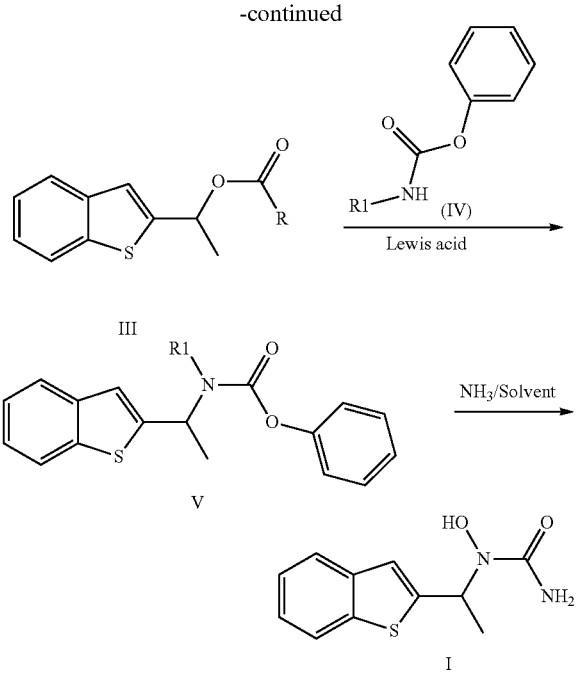

Wherein
R = Me, Et, Ph
R1 = OH, O(CO)O—Ph
X = Cl, Br, F, I

The present invention is described by the following examples, which are for illustrative purpose only and should not be construed as to limit the scope of the invention in any manner.

Example-1

Preparation of 1-Benzo[b]thiophen-2-yl-ethanol (II)

An aqueous solution of sodium borohydride[Sodium borohydride (15.3 gm) dissolved in water (60 ml)] was added to a slurry of 2-acetyl benzothiophene (100 gm) and methanol (300 ml) and cooled at 5-10° C. and maintained for 2 hrs at the same temperature. The progress of the reaction was monitored by HPLC. After completion of the reaction, the pH of the reaction mass was adjusted to 7.0-7.5 using Con. HCl and distilled under the reduced pressure. The resultant mass was added into water (700 ml) and stirred for 2 hrs. The resultant solid was filtered and washed with water (200 ml). % Yield: 90%.

Example-2

Preparation of Acetic acid 1-benzo[b]thiophen-2-yl-ethyl ester (III)

The solid obtained in example-1 (1-Benzo[b]thiophen-2-yl-ethanol) was dissolved in 900 ml of toluene, followed by the addition of water. The toluene layer was separated from the resultant biphasic mixture, and washed with 10% brine solution (750 ml). The washed toluene layer was cooled to 0-5° C. and followed by the addition of triethyl amine (187.6 ml) and dimethylaminopyridine (DMAP) (5.14 gm). Acetic anhydride (120 ml) was slowly added to the resultant reaction mixture and stirred for 2 hrs at 25-30° C. The progress of the reaction was monitored by HPLC. After completion of the reaction, the reaction mass was washed with water (750 ml); then with 10% acetic acid (750 ml) and followed by 10% of brine solution (750 ml). The resultant organic phase is taken for the next step without isolation. % Yield: 95%

Example 3

Preparation of N-(phenyl hydroxyl carbamate) (IV)

Sodium bicarbonate (128.7 gm) was added to aqueous solution of hydroxylamine hydrochloride [hydroxylamine hydrochloride (50.0 gm) in water (400 ml)] at 30° C. followed by ethyl acetate (600 ml) and cooled to 5-10° C. To this mixture phenyl chloroformate (100 gm) was added slowly at 5-10° C. and stirred for about 2 hrs for 30° C. The progress of the reaction was monitored by HPLC. After completion of the reaction, ethyl acetate layer was separated and distilled under reduced pressure to an oily mass. The oily mass was mixed with cyclohexane (600 ml) at 60° C. and distilled out at 75-80° C. The resultant mass brought to 30° C., then stirred for about 2 hrs. The resulted solid was filtered, washed with cyclohexane (200 ml) and dried under vacuum. Yield: 85%.

Example-4

Preparation of N, O-Bis-(phenoxy carbonyl) hydroxyl-amine (IVa)

Hydroxylamine hydrochloride (60.0 gm) was added to aqueous solution of Sodium carbonate [Sodium bicarbonate (146.5 gm) in water (1022 ml)] at 0-5° C. followed by a slow addition of phenyl chloroformate (262 gm), then the reaction mixture was stirred for 15 mins at the same temperature. The progress of the reaction was monitored by HPLC. After completion of the reaction, an aqueous solution of Sodium bicarbonate [Sodium bicarbonate (219.6 gm) in water (1803 ml)] was added to the reaction mass followed by water (204 ml) at 0-5° C. and then raised to 25° C. Diisopropyl ether (1200 ml) was added to the reaction mass to form a biphasic mixture. The Organic layer was separated, distilled to obtain a concentrated mass. The concentrated was was mixed with n-heptane (1200 ml) and stirred for 12 hrs at 25-30° C. The contents were cooled to 0-5° C. and stirred for one hr. The resulted solid obtained was filtered, washed with chilled n-heptane (120 ml) and dried under vacuum. HPLC purity: 95% Yield: 90%

Example-5

Preparation of phenyl 1-(benzo[b]thiophen-2-yl)ethyl(hydroxyl) carbamate (V)

The organic phase obtained in Example-2, phenyl N-hydroxy carbamate (141.7 gm) was added and cooled to 5-10° C. Boron trifluoride dietherate (18.75 gm) was slowly added to the mixture at 25-30° C. for 2 hrs. The progress of the reaction was monitored by HPLC. After completion of the reaction, water (900 ml) was added to the reaction mass and stirred. The contents were cooled to 0-5° C., filtered, washed with cyclohexane and dried. % Yield: 85%

Example-6

Preparation of phenyl N,O-Bis(phenoxycarbonyl)-N-(1-benzo[b]thien-2-ylethy1) hydroxylamine (Va)

A mixture of the solid obtained in Example-2 (100 gm), toluene (1000 ml), N, O-Bis-(phenoxy carbonyl) hydroxylamine (155.05 gm) was stirred to form clear solution and then cooled to 5-10° C. Borontrifluoride-dietherate 50% solution, (25.0 gm) was slowly added to the reaction mixture and stirred at 5-10° C. for 1 hr. The progress of the reaction was monitored by HPLC. After completion of the reaction, water (1000 ml) was added into a reaction mass and stirred. The organic and aqueous layers were separated. The organic layer was separated and distilled under reduced pressure to obtain a residue. HPLC purity: 98% Yield: 95%

Example-7

Preparation of Crude Zileuton (I)

A mixture of solid obtained in Example-5 (50 gm), dimethylformamide (200 ml) and water (100 ml of process) was charged in an autoclave. Ammonia was pressurized to 5 kg/cm² in the autoclave and stirred for 5 hr at 30-35° C. The progress of the reaction was monitored by HPLC. After completion of the reaction, the reaction mass was added to water (500 ml) and stirred for 4 hrs at 30-35° C. The contents were then filtered, washed with water (100 ml) and dried under vacuum. % Yield: 65%

Example-7A

Preparation of Crude Zileuton (I)

A mixture of solid obtained in Example-6 (50 gm) and methanol (500 ml) was charged in an autoclave. Ammonia pressurized to 5 kg/cm² in the autoclave and stirred for 5 hrs at 30-35° C. The progress of the reaction was monitored by HPLC, after completion of the reaction, the reaction mass was added to diisopropyl ether (250 ml) and stirred for stirred for 1 hr. The contents were then filtered, washed with Diisopropyl ether (25 ml) and dried under vacuum. % Yield: 75%

Example-7B

Preparation of crude Zileuton (I)

A mixture obtained in Example-5 (50 gm), dimethylformamide (100 ml) and aqueous ammonia (200 ml of process) was charged in an autoclave and cooled to 15° C. Ammonia gas was pressurized at 3-3.5 kg/cm² into the reaction mass and maintained for 10 hr at 30-35° C. The progress of the reaction was monitored by HPLC. After completion of the reaction, the reaction mass was added to water (500 ml) and stirred for 4 hr at 30-35° C. The contents were then filtered, washed with water (100 ml) and further purified by charging the wet cake in to water (500 ml) at 30-35° C. The pH was adjusted with 25% NaOH solution to 13.0-13.5 and washed with MTBE (200 ml) 3 times. The content was cooled to 12-15° C. and acidified to pH 10-11 using conc. HCl and stirred for 2 hr at 12-15° C. The solid was filtered at 12-15° C. and washed with water (125 ml) followed by cyclohexane (125 ml). The product was suck dried well for 2.5-3.0 hrs and then dried under vacuum at 55° C. The dried product was further purified by charging into toluene (300 ml) as slurry and heated to 40° C. for 2 hr, than cooled to 30° C. for 2 hr. The product obtained was filtered, washed with toluene (50 ml), and dried under vacuum at 50° C. Yield: 70%

Example-8

Purification of Zileuton (I)

The Crude Zileuton (50 gm) resulted in Example-7 was suspended in ethyl acetate (1000 ml) and heated to 70-75° C. for about 15 minutes to get a clear solution. Activated carbon (5 gm) was added to the resulted solution and stirred for 1 hr at 70-75° C. The contents were filtered through hyflow at 60° C. and concentrated under reduced pressure to obtain a residue. This obtained residue was mixed with ethyl acetate (100 ml) and stirred for 15 minutes. The contents were then cooled to 5-10° C. and stirred for 1 hr. The contents were filtered, and dried.

Example-8A

Purification of Zileuton (I)

The Crude Zileuton (50 gm) obtained in Example-7B was suspended in acetone (1000 ml) at 30° C. and stirred to get a clear solution. Activated Charcoal (10 gm) was charged at 30° C. into the solution and stirred for 1 h. The content was filtered through Hyflo to remove carbon followed by 0.2 micron filtration. The acetone was distilled off from the filtrate to get stirrable pasty mass and methyl-tertiary butyl ether (MTBE) (500 ml) was charged in to pasty mass and stirred at 35-40° C. for 0.5 hr. MTBE was distilled off at 35° C. to get stirrable pasty mass and ethyl acetate (100 ml) was charged into this at 30±5° C. and stirred for 0.5 hr and then cooled to 3-5° C. for 2 hr. The solid obtained was filtered, washed with 50 ml of chilledethyl acetate and dried under vacuum at 50° C. Yield: 80-85%.

We claim:
1. A process for preparing Zileuton of formula-I

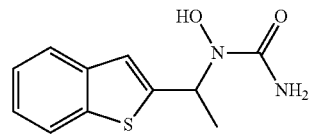

comprising the steps of:
(i) reacting 1-benzo[b]thiophen-2-yl-ethanol compound of formula II

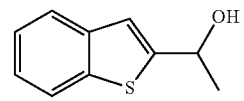

with anhydride of general formula (RCO)₂O or acyl halide of general formula (RCOX) to obtained 1-benzo[b]thiophen-2-yl-ethyl-ester of formula-III

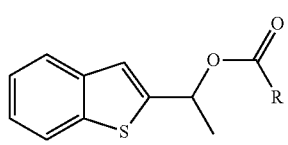

in presence of a base and solvent
wherein R is methyl, ethyl or phenyl and X is halogen selected from fluoride, choride, bromide and iodide;

(ii) reacting 1-benzo[b]thiophen-2-yl-ethyl-ester compound of formula-III obtained in step (i) with phenyl-N-hydroxy carbamate of formula-IV

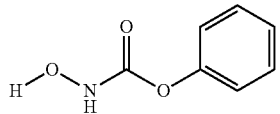

IV in the presence of a Lewis acid to obtain phenyl-1-(benzo[b]thiophen-2-yl)ethyl(hydroxyl)carbamate of formula V;

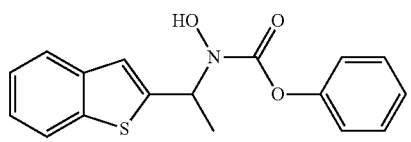

V (iii) optionally, purifying the compound of formula V using a solvent to provide pure phenyl-1-(benzo[b]thiophen-2-yl)ethyl(hydroxyl)carbamate of formula V; and
(iv) treating phenyl-1-(benzo[b]thiophen-2-yl)ethyl(hydroxyl)carbamate compound of formula-V with ammonia to obtain Zileuton of formula I.
2. A process for preparing Zileuton of formula-I;

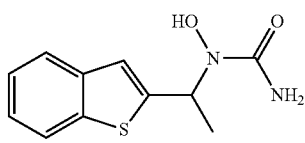

I comprising the steps of;
(i) reacting 1-benzo[b]thiophen-2-yl-ethanol compound of formula II

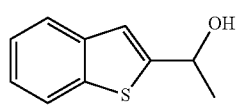

II with anhydride of general formula $(RCO)_2O$ in presence of a base and non-polar aprotic solvent to obtained 1-benzo[b]thiophen-2-yl-ethyl-ester of formula-III

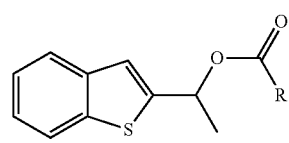

III wherein R is methyl, ethyl or phenyl;
(ii) reacting the 1-benzo[b]thiophen-2-yl-ethyl-ester compound of formula-III obtained step (i) with N,O-bis-(phenoxy carbonyl) hydroxyl-amine of formula-IVa

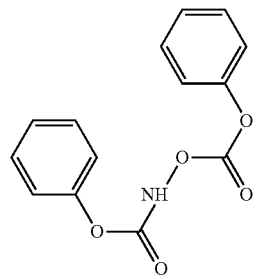

IVa in the presence of a Lewis acid to obtain phenyl N, O-Bis(phenoxycarbonyl)-N-(1-benzo[b] thien-2-yl-ethyl) hydroxylamine of formula Va;

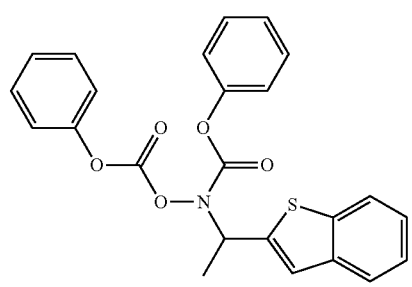

Va (iii) optionally, purifying the compound of formula Va using a solvent to provide pure compound of formula Va; and
(iv) treating phenyl N, O-bis(phenoxycarbonyl)-N-(1-benzo[b] thien-2-ylethyl) hydroxylamine of formula Va with ammonia to obtain Zileuton of formula I.

3. The process according to claim 1, wherein the base of step (i) is dimethylaminopyridine (DMAP).

4. The process according to claim 1, wherein the solvent in step (i) is selected from the group consisting of benzene, toluene, xylene, tetrahydrofuran and 2-methyltetrahydrofuran.

5. The process according to claim 4, wherein the solvent is toluene.

6. The process according to claim 1, wherein the Lewis acid in step (ii) is selected from the group comprising of aluminum bromide, aluminum chloride, boron trifluoride, boron trichloride, boron trifluoride-diethyletherate, boron tribromide, titanium tetrachloride, titanium tetrabromide, stannic chloride, stannic bromide, bismuth trichloride and ferric chloride.

7. The process according to claim 6, wherein the Lewis acid is boron trifluoride-diethyletherate.

8. The process according to claim 1, wherein in step (iii) the optional purification is carried out by contacting compound of formula V or Va with non-polar organic solvents selected from the group comprising of benzene, toluene, xylene, tetrahydrofuran, n-hexane and cyclohexane.

9. The process according to claim 8, wherein the non-polar organic solvent is cyclohexane.

10. The process according to claim 1, wherein step (iv) is performed in a polar aprotic solvent selected from the group comprising of dimethylformamide, acetone, ethyl acetate, tetrahydrofuran, acetonitrile, dimethylsulfoxide, nitromethane and propylene carbonate or mixture thereof with water.

11. The process according to claim 10, wherein the polar aprotic solvent is Dimethylformamide.

12. A process for preparing Zileuton of formula-I,

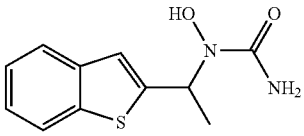

comprising the steps of;
(i) reacting 1-Benzo[b]thiophen-2-yl-ethanol compound of formula II

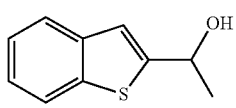

with acetic anhydride in presence of dimethylaminopyridine (DMAP) base and toluene as reaction solvent to obtained acetic acid-1-benzo[b]thiophen-2-yl-ethyl-ester of formula-III

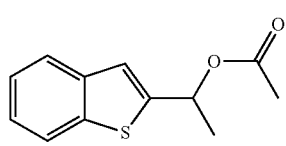

(ii) reacting the acetic acid-1-benzo[b]thiophen-2-yl-ethyl-ester of formula-III with phenyl-N-hydroxy carbamate of formula-IV

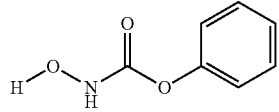

in the presence of boron trifluoride-diethyletherate to obtain phenyl-1-(benzo[b]thiophen-2-yl)ethyl(hydroxyl)carbamate of formula V;

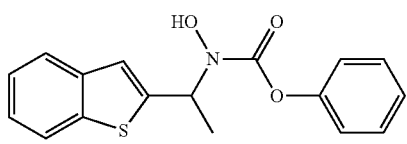

(iii) purifying the compound of formula V by employing suitable solvent to provide pure compound of formula V; and
(iv) treating pure phenyl-1-(benzo[b] thiophen-2-yl)ethyl (hydroxyl)carbamate of compound formula-V with ammonia in suitable solvent to obtain Zileuton of formula I.

13. A process for preparing Zileuton of formula I

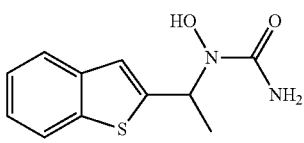

comprising the steps of:
(i) reacting acetic acid-1-benzo[b]thiophen-2-yl-ethyl-ester of formula-III

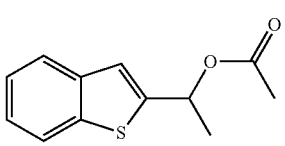

with phenyl-N-hydroxy carbamate of formula-IV

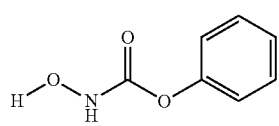

in the presence of boron trifluoride-diethyletherate to obtain phenyl-1-(benzo[b]thiophen-2-yl)ethyl(hydroxyl)carbamate of formula V; and
(ii) treating the phenyl-1-(benzo[b]thiophen-2-yl)ethyl (hydroxyl)carbamate of formula-V

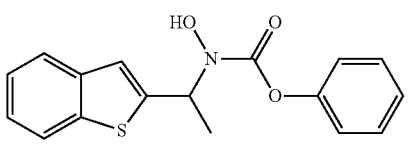

with ammonia in a suitable solvent to obtain Zileuton of formula I.

14. The process according to claim 12, wherein the suitable solvent is selected from the group comprising of dimethylformamide, acetone, ethyl acetate, tetrahydrofuran, acetonitrile, dimethylsulfoxide, nitromethane and propylene carbonate or mixture thereof in presence of absence of water.

15. A process for preparing Zileuton of formula I comprising, treating phenyl-1-(benzo[b]thiophen-2-yl)ethyl(hydroxyl)carbamate of formula-V

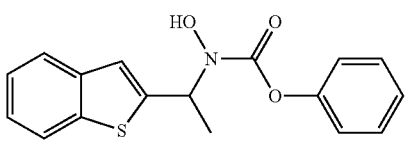

with ammonia in a polar aprotic solvent to obtain Zileuton of formula I.

16. The process according to claim 15, wherein the polar aprotic solvent is selected from the group comprising of dimethylformamide, acetone, ethyl acetate, tetrahydrofuran, acetonitrile, dimethylsulfoxide, nitromethane and propylene carbonate or mixture thereof in presence or absence of water.

17. The process according to claim 16, wherein the polar aprotic solvent is dimethylformamide.

18. A process for preparing Zileuton of formula-I

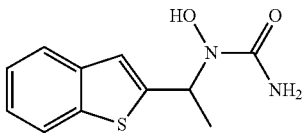

comprising the steps of:
(i) reacting 1-benzo[b]thiophen-2-yl-ethanol compound of formula II

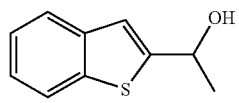

with acetic anhydride in presence of base in a non-polar aprotic solvent and extracting acetic acid-1-benzo[b]thiophen-2-yl-ethyl-ester of formula-III in organic phase;

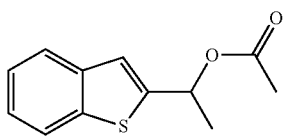

(ii) treating organic phase of step (i) containing acetic acid-1-benzo[b]thiophen-2-yl-ethyl-ester of formula-III with phenyl-N-hydroxy carbamate of formula-IV

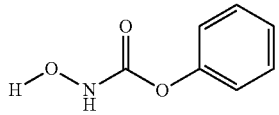

in the presence of boron trifluoride-diethyletherate to obtain phenyl-1-(benzo[b]thiophen-2-yl)ethyl(hydroxyl)carbamate of formula V;

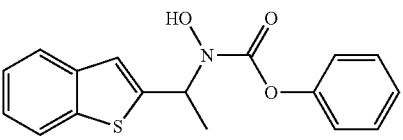

(iii) purifying the compound of formula Va using a suitable solvent to provide pure compound of formula Va; and
(iv) treating compound phenyl-1-(benzo[b]thiophen-2-yl) ethyl(hydroxyl)carbamate of formula-V with ammonia in suitable solvent to obtain Zileuton of formula I.

19. The process according to claim 18, wherein in step (iii) the suitable solvent is cyclohexane.

20. The process according to claim 18, wherein in step (iv) the suitable solvent is dimethylformamide in presence of water.

* * * * *

UNITED STATES PATENT AND TRADEMARK OFFICE
CERTIFICATE OF CORRECTION

PATENT NO. : 9,670,176 B2
APPLICATION NO. : 15/193385
DATED : June 6, 2017
INVENTOR(S) : Sankar Arjunan et al.

It is certified that error appears in the above-identified patent and that said Letters Patent is hereby corrected as shown below:

In the Claims

Column 18, Line 67, Claim 1, delete "choride," and insert -- chloride, --

Column 21, Line 64, Claim 12, delete "[b] thiophen" and insert -- [b]thiophen --

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*